United States Patent [19]
Leonard

[11] Patent Number: 5,762,868
[45] Date of Patent: Jun. 9, 1998

[54] BLOOD OXYGENATOR AND HEAT EXCHANGER

[75] Inventor: Ronald J. Leonard, Ann Arbor, Mich.

[73] Assignee: Minnesota Mining and Manufacturing Company, St. Paul, Minn.

[21] Appl. No.: 565,438

[22] Filed: Nov. 30, 1995

[51] Int. Cl.$^6$ .............................. A61M 1/14; A61M 1/34
[52] U.S. Cl. ..................... 422/46; 422/48; 604/4; 604/5; 604/406; 428/372
[58] Field of Search ................. 422/46, 48; 210/321.6, 210/321.89, 500.23, 500.26; 604/4, 5, 406; 428/372; 96/10, 6

[56] References Cited

U.S. PATENT DOCUMENTS

| | | | |
|---|---|---|---|
| 2,217,370 | 10/1940 | Johnston | 166/7 |
| 3,211,148 | 10/1965 | Galajda, Jr. | 128/214 |
| 3,339,341 | 9/1967 | Maxwell et al. | 55/16 |

(List continued on next page.)

FOREIGN PATENT DOCUMENTS

| | | |
|---|---|---|
| 0 041 467 | 12/1981 | European Pat. Off. . |
| 0 093 677 | 11/1983 | European Pat. Off. . |
| 0 285 812 | 10/1993 | European Pat. Off. . |
| 2 300 312 | 7/1973 | Germany . |
| 24 41 333 | 3/1975 | Germany . |
| 27 21 444 | 11/1978 | Germany . |
| 79 11 220 | 4/1979 | Germany . |
| 28 25 065 | 12/1979 | Germany . |
| 207 607 | 3/1984 | Germany . |
| 32 36 946 | 4/1984 | Germany . |
| 233 946 | 3/1986 | Germany . |
| 49-55569 | 5/1974 | Japan . |
| 52-38836 | 10/1977 | Japan . |
| 53-39695 | 4/1978 | Japan . |
| 54-136579 | 10/1979 | Japan . |
| 56-78601 | 6/1981 | Japan . |
| 57-53205 | 3/1982 | Japan . |
| 58-155862 | 9/1983 | Japan . |
| 59-11866 | 1/1984 | Japan . |
| 62-57965 | 3/1987 | Japan . |
| 62-72364 | 4/1987 | Japan . |
| 1-176405 | 7/1989 | Japan . |
| 2-172522 | 7/1990 | Japan . |
| 4-2066 | 1/1992 | Japan . |
| 1 481 064 | 7/1977 | United Kingdom . |
| WO 83/00098 | 1/1983 | WIPO . |
| WO 90/07943 | 7/1990 | WIPO . |
| WO 95/11709 | 5/1995 | WIPO . |

OTHER PUBLICATIONS

Brochure entitled "Sarns® SMO/INF Infant Membrane Oxygenator-Instructions", 3M; Dec. 1989; Form No. 16499401 R/D.

Brochure entitled "Sarns® SMO/IR Membrane Oxygenator with Integral Reservoir-Instructions"; 3M; Mar. . 1990; Form No. 34-9998-9113-7 R/A.

Flyer entitled "SMO/IR Sarns Membrane Oxygenator with Integral Resrvoir"; 3M. 1990; Form No. 78-8066-9350-9.

Flyer entitled "SMO/INF Sarns Infant Membrane Oxygenator", 3M, 1990; Form No. 78-8066-9351-7.

(List continued on next page.)

*Primary Examiner*—Nina Bhat
*Attorney, Agent, or Firm*—Gary L. Griswold; Walter N. Kirn; Stephen W. Bauer

[57] ABSTRACT

An integral blood oxygenator and heat exchanger device for oxygenating and heating or cooling a patient's blood during heart bypass surgery. The device preferably includes a pleated blood filter disposed within a gap formed between the opposite ends of the blood oxygenating medium. A blood inlet manifold closely receives a tubular heat exchanging barrier and directs blood flow around the barrier to a blood outlet slot. The blood oxygenating medium covers the blood outlet slot so that blood must flow through the blood oxygenating medium before reaching the blood filter. A vent port and bypass port may be provided in the gap formed by the opposite ends of the blood oxygenating medium upstream of the blood filter.

25 Claims, 8 Drawing Sheets

U.S. PATENT DOCUMENTS

| | | | |
|---|---|---|---|
| 3,412,865 | 11/1968 | Lontz et al. | 210/321 |
| 3,422,008 | 1/1969 | McLain | 210/22 |
| 3,468,631 | 9/1969 | Raible et al. | 23/258.2 |
| 3,489,647 | 1/1970 | Kolobow | 195/1.8 |
| 3,536,611 | 10/1970 | Filippi et al. | 210/22 |
| 3,615,238 | 10/1971 | Bentley | 23/258.5 |
| 3,690,465 | 9/1972 | McGinnis et al. | 210/321 |
| 3,757,955 | 9/1973 | Leonard | 210/321 |
| 3,794,468 | 2/1974 | Leonard | 23/258.5 |
| 3,879,293 | 4/1975 | Wolf, Jr. et al. | 210/321 |
| 3,890,969 | 6/1975 | Fischel | 128/214 |
| 3,927,980 | 12/1975 | Leonard | 23/258.5 |
| 3,929,414 | 12/1975 | Leonard | 23/258.5 |
| 3,989,626 | 11/1976 | Bentley et al. | 210/177 |
| 4,022,692 | 5/1977 | Janneck | 210/321 |
| 4,045,851 | 9/1977 | Ashare et al. | 29/157 |
| 4,061,470 | 12/1977 | Leonard | 23/258.5 |
| 4,140,637 | 2/1979 | Walter | 210/321 |
| 4,151,088 | 4/1979 | Wolf, Jr. et al. | 210/180 |
| 4,172,794 | 10/1979 | Sigdell | 210/232 |
| 4,188,360 | 2/1980 | Kurata | 422/46 |
| 4,205,042 | 5/1980 | Lobdell et al. | 422/47 |
| 4,213,858 | 7/1980 | Boberg et al. | 210/23 |
| 4,227,295 | 10/1980 | Bodnar et al. | 29/527.3 |
| 4,256,692 | 3/1981 | Cover | 422/46 |
| 4,301,013 | 11/1981 | Setti et al. | 210/637 |
| 4,315,819 | 2/1982 | King et al. | 210/321.3 |
| 4,343,668 | 8/1982 | Francisoud et al. | 156/172 |
| 4,346,006 | 8/1982 | Kopp et al. | 210/321.4 |
| 4,350,549 | 9/1982 | Frohner | 156/161 |
| 4,401,431 | 8/1983 | Arp | 604/4 |
| 4,424,190 | 1/1984 | Mather, III et al. | 422/46 |
| 4,430,219 | 2/1984 | Kuzumoto et al. | 210/321.3 |
| 4,451,562 | 5/1984 | Elgas et al. | 435/2 |
| 4,469,659 | 9/1984 | Carson et al. | 422/46 |
| 4,533,089 | 8/1985 | Sartor et al. | 242/7.21 |
| 4,559,999 | 12/1985 | Servas et al. | 165/156 |
| 4,572,446 | 2/1986 | Leonard et al. | 242/7.02 |
| 4,639,353 | 1/1987 | Takemura et al. | 422/46 |
| 4,659,549 | 4/1987 | Hamada et al. | 422/48 |
| 4,689,255 | 8/1987 | Smoot et al. | 428/77 |
| 4,690,758 | 9/1987 | Leonard et al. | 210/247 |
| 4,715,953 | 12/1987 | Leonard | 210/321.8 |
| 4,735,775 | 4/1988 | Leonard et al. | 422/46 |
| 4,770,852 | 9/1988 | Takahara et al. | 422/48 |
| 4,791,054 | 12/1988 | Hamada et al. | 435/2 |
| 4,818,490 | 4/1989 | Carson et al. | 422/46 |
| 4,846,177 | 7/1989 | Leonard | 128/400 |
| 4,902,416 | 2/1990 | Schroeder et al. | 210/321 |
| 4,906,372 | 3/1990 | Hopkins | 210/321 |
| 4,940,617 | 7/1990 | Baurmeister | 428/36.3 |
| 4,952,312 | 8/1990 | Zantonelli et al. | 210/321 |
| 4,971,836 | 11/1990 | Fukasawa et al. | 427/235 |
| 4,975,247 | 12/1990 | Badolato et al. | 422/48 |
| 5,015,379 | 5/1991 | Drori | 210/411 |
| 5,026,479 | 6/1991 | Bikson et al. | 210/321.8 |
| 5,039,482 | 8/1991 | Panzani et al. | 422/46 |
| 5,043,140 | 8/1991 | Combs | 422/46 |
| 5,102,533 | 4/1992 | Oshiyama | 210/85 |
| 5,139,529 | 8/1992 | Seita et al. | 623/66 |
| 5,139,741 | 8/1992 | Hagiwara | 422/48 |
| 5,143,312 | 9/1992 | Baurmeister | 242/7 |
| 5,152,964 | 10/1992 | Leonard | 422/48 |
| 5,158,533 | 10/1992 | Strauss et al. | 604/4 |
| 5,160,672 | 11/1992 | Sasaki et al. | 264/41 |
| 5,186,835 | 2/1993 | Masuoka et al. | 210/500 |
| 5,188,801 | 2/1993 | Fini | 422/48 |
| 5,192,499 | 3/1993 | Sakai et al. | 422/46 |
| 5,202,025 | 4/1993 | Onishi et al. | 210/500 |
| 5,225,161 | 7/1993 | Mathewson et al. | 422/46 |
| 5,236,665 | 8/1993 | Mathewson et al. | 422/46 |
| 5,240,677 | 8/1993 | Jones et al. | 422/46 |
| 5,255,734 | 10/1993 | Leonard et al. | 165/96 |
| 5,266,265 | 11/1993 | Raible | 422/46 |
| 5,270,004 | 12/1993 | Cosentino et al. | 422/46 |
| 5,270,005 | 12/1993 | Raible | 422/46 |
| 5,279,738 | 1/1994 | Seita et al. | 210/500 |
| 5,284,584 | 2/1994 | Huang et al. | 210/321 |
| 5,294,401 | 3/1994 | Hagiwara | 422/48 |
| 5,304,164 | 4/1994 | Lindsay | 604/403 |
| 5,312,589 | 5/1994 | Reeder et al. | 422/45 |
| 5,346,621 | 9/1994 | Haworth et al. | 210/645 |
| 5,376,334 | 12/1994 | Haworth et al. | 422/46 |
| 5,382,407 | 1/1995 | Leonard | 422/48 |
| 5,411,705 | 5/1995 | Thor et al. | 422/45 |
| 5,421,405 | 6/1995 | Goodin et al. | 165/154 |
| 5,462,619 | 10/1995 | Haworth et al. | 156/172 |
| 5,489,382 | 2/1996 | Tatebe et al. | 210/321 |
| 5,489,413 | 2/1996 | Carson et al. | 422/46 |

OTHER PUBLICATIONS

Brochure entitled "When you bring efficiency to the surface . . . you can lower the prime."; 3M; 1990; Form No. 16088004 Rev.B.

Flyer entitled "SMO/ICR Sarns Membrane Oxygenator with Integral Cardiotomy Reservoir ". 3M 1990; Form No. 78–8066–9349–1.

Mockros et al.; "Compact Cross–Flow Tubular Oxygenators"; vol. XXXI. Trans. Am Soc. Artif Intern Organs 1985.

"Processes and Units for Reverse Osmosis and Ion Exchange"; Hollow Fibers–Manufacture and Applications; Chemical Technology Review No. 194; 1981.

Brochure entitled "the Travenol TMO membrane oxygenator"; Artificial Organs Division of Travenol Laboratories, Inc. Jan. 1977 (10 pages).

Brochure entitled "Travenol TMO membrane oxygenator—Improved for consistent performance . . . ". Travenol Laboratories, Inc. Artificial Organs Division Jan. 1979 (8 pages).

Brochure entitled "TMO Oxygenator Integrated Circuit System—passes the test of time"; Cardiopulmonary Products, Travenol Laboratories, Inc.; 1982 (4 pages).

Brochure entitled "The new alternative to bubble oxygenators from TRAVENOL"; Travenol Laboratories Inc.. Cardiopulmonary Products; 1982 (5 pages).

Brochure entitled "Travenol –code 5M1431 –LPM/50 Membrane Oxygenator—Low Pressure Adult Oxygenator with Integral Heat Exchanger and Reservoir—Directions for Use"; Travenol Laboratories Inc.; Jan. 1982 (18 pages).

Brochure entitled "Rhone–Poulenc Genie Medical—L'oxygenateur a Membrane M 3". Medical Department Genie Medical, Paris, 74 B 6333 (4 pages).

Brochure "Description of the M 3 Oxygenators" Hospal, Paris; 1979 (some translation) (21 pages).

Brochure "Choisissez La Securite . . . Oxygenateurs—Opal—M4"; Hospal France; (5 pages).

BLOOD OXYGENATOR AND HEAT EXCHANGER

This application relates to a blood oxygenator and heat exchanger of the type used for extracorporeal circulatory support.

BACKGROUND OF THE INVENTION

Over the years, a quest in the technology of membrane blood oxygenation has been to provide higher and more uniform gas transfer performance at ever lower prime volumes. This is still the goal, but in addition, reduced surface area for better biocompatibility, low pressure drop and improved biocompatibility through flow improvements, both within the active elements (e.g., blood oxygenating medium) and within distribution manifolding are believed to be important. In addition, reduced overall size is now desirable in the ever more crowded operating room.

Examples of prior membrane blood oxygenator and heat exchanger devices are shown in U.S. Pat. Nos. 3,757,955; 3,794,468; 3,879,293; 3,927,980; 3,929,414; 4,061,470; 4,151,088; 4,572,446; 4,690,758; 4,735,775; 5,152,964; 5,255,734; 5,304,164 and 5,382,407. Co-assigned PCT international patent publication No. WO 95/11709 discloses a blood oxygenation system and reservoir and method of manufacture.

SUMMARY OF THE INVENTION

This invention provides an integral blood oxygenator and heat exchanger ("device") for oxygenating and heating or cooling a patient's blood during heart bypass surgery. The integral blood oxygenator and heat exchanger is designed to reduce the amount of blood or priming solution required to prime the device while maintaining efficient and reliable oxygenation and heating or cooling of blood passing through the device. The device is further designed to promote mixing of blood through the oxygenating medium without excessive pressure loss.

The integral blood oxygenator and heat exchanger is also arranged to maintain a distributed pattern of blood flow through the heat exchanger, blood oxygenating medium, and preferably an integral blood filtering medium, without intervening collection and distribution manifolds between the heat exchanger, blood oxygenating medium and blood filtering medium. Blood flows substantially directly from the heat exchanger portion of the device to the oxygenating portion and then substantially directly to the filter portion.

The integral blood oxygenator and heat exchanger has further been designed in an effort to minimize hemolysis and the risk of thrombosis generation to reduce the amount of systemic heparin that is administered to patients undergoing heart bypass operations.

In addition, the integral blood oxygenator and heat exchanger is designed to be relatively compact so that it requires less space within the increasingly crowded operating room and less space when held in inventory.

Generally, the integral blood oxygenator and heat exchanger of the invention comprises a generally elongate, generally tubular heat exchanger barrier for separating blood and heat-exchanging fluid while permitting heat transfer across the barrier; and a generally elongate inlet manifold closely receiving the heat exchanger barrier. The inlet manifold defines a blood inlet passageway extending longitudinally along one side of the heat exchanger barrier, and a blood outlet slot extending generally longitudinally along

2 the opposite side of the heat exchanger barrier. The blood inlet passageway and blood outlet slot define a blood flow passageway extending generally circumferentially around the heat exchanger barrier. A blood oxygenating medium is provided comprising a plurality of plies of a mat. Each ply comprises porous hollow fibers through which oxygen flows to oxygenate blood flowing around the hollow fibers. The blood oxygenating medium is wrapped around the inlet manifold so that blood exiting the outlet slot must flow through the oxygenating medium. A housing closely receives the oxygenating medium, manifold and heat exchanger barrier. The housing defines an outlet manifold extending longitudinally along one side of the housing generally opposite the blood outlet slot of the inlet manifold, thereby defining a blood flow path through the blood oxygenating medium extending around the inlet manifold between the blood outlet slot of the inlet manifold and the outlet manifold of the housing. The housing has a blood outlet in fluid communication with the outlet manifold and a blood inlet in fluid communication with the blood inlet passageway of the inlet manifold.

Preferably, the blood oxygenating medium has opposite ends defining a gap extending longitudinally along the side of the inlet manifold generally opposite the blood outlet slot, and a blood filtering medium is disposed within the gap so that blood is filtered before the blood exits the housing through the outlet manifold and blood outlet. The blood filtering medium may comprise a pleated filter element A bypass means may optionally be provided for bypassing the blood filtering medium if the blood filtering medium becomes clogged to allow blood to exit the housing without passing through the blood filtering medium. For example, the bypass means may comprise a bypass port on the housing in fluid communication with the gap between the opposite ends of the blood oxygenating medium and the blood filtering medium.

Most preferably, at least one vent port is provided on the housing in fluid communication with the gap between the opposite ends of the blood oxygenating medium and the blood filtering medium for venting gas upstream of the blood filtering medium.

Also, preferably, the mat comprises a single hollow fiber mat. The porous hollow fibers comprise a plurality of hollow fibers disposed at regular intervals, and a plurality of connecting fibers are provided to hold the hollow fibers. The mat is repeatedly folded over on itself along fold lines, each of which is at an oblique angle (e.g., 1–15 degrees) to the hollow fibers, to form a multilayer hollow fiber body in which the hollow fibers of any ply of the multilayer hollow fiber body are disposed so as to cross the hollow fibers of an adjacent successive ply of the multilayer hollow fiber body.

Most preferably, the mat is generally elongate, and the hollow fibers extend at an oblique angle (e.g., 75–89 degrees) with respect to the direction of elongation of the mat. The fold lines are generally parallel to one another and generally perpendicular to the direction of elongation of the mat. The connecting fibers are disposed at regular intervals and extend generally in the direction of elongation of the mat. The connecting fibers are interweaved with the hollow fibers to hold the fibers in the mat.

Also, preferably, the distance between the fold lines along any ply is the same as the distance between the fold lines along any other ply. This arrangement is such that, when the multilayer hollow fiber body is wrapped around the inlet manifold, the plies progressively leave a wider gap between the opposite ends in the direction outwardly from the inlet manifold toward the housing. This arrangement also provides a more uniform length blood flow path through the blood oxygenating medium, that is, blood flowing through the blood oxygenating medium near the internal wall of the housing flows about the same distance as blood flowing near the outer wall of the inlet manifold.

The heat exchanger barrier preferably comprises a generally tubular metallic barrier having an undulating wall defining a plurality of channels that together form the blood flow passageway. The plurality of channels extend generally circumferentially around the metallic barrier, and the inlet manifold closely receives the heat exchanger barrier so that the blood flow passageway is substantially restricted to the channels.

In a second aspect of the invention, an integral blood oxygenator, heat exchanger and blood filter device generally comprises a heat exchanger barrier for separating blood and heat-exchanging fluid while permitting heat transfer across the barrier; a manifold receiving the heat exchanger barrier, the manifold defining a blood inlet and a blood outlet defining a blood flow passageway extending along the heat exchanger barrier; a blood oxygenating medium wrapped around the manifold so that blood flow through the outlet of the manifold must pass through the blood oxygenating medium, the blood oxygenating medium having opposite ends defining a gap between the ends along the outside of the manifold; and a blood filtering medium disposed within the gap between the opposite end of the blood oxygenating medium to filter blood exiting the blood oxygenating medium, the blood filtering medium having upstream and downstream sides. A housing is provided for the blood filtering medium, blood oxygenating medium, manifold and heat exchanger barrier. The housing has a blood outlet in fluid communication with the downstream side of the blood filtering medium, thereby defining a blood flow path through the blood oxygenating medium and blood filtering medium extending around the manifold between the blood outlet of the manifold and the blood outlet of the housing.

Preferably, the blood oxygenating medium covers the outlet of the manifold.

Blood exits the blood oxygenating medium through the opposite ends of the oxygenating medium, traveling in the same general direction in which the blood traveled through the blood oxygenating medium.

Additional features will be pointed out hereinafter.

BRIEF DESCRIPTION OF THE DRAWING

The invention will be further described with reference to the drawing, wherein corresponding reference characters indicate corresponding parts throughout the several views of the drawing, and wherein.

DETAILED DESCRIPTION OF PREFERRED EMBODIMENTS

Now referring to the drawings, an integral blood oxygenator, heat exchanger and blood filter device of the invention is designated in its entirety by the reference numeral 20. The integral blood oxygenator and heat exchanger device 20 is useful for oxygenating and heating or cooling a patient's blood during heart bypass surgery. As used herein, the term "longitudinal direction" of the device 20 means major direction of elongation of the device shown in the drawings, i.e., the vertical direction in FIGS. 1, 2 and 7. Many of the features of the invention and their relationship are illustrated in cross-sectional FIG. 5. Cross-sectional FIGS. 6 and 7 also illustrate internal aspects of the blood oxygenator and heat exchanger of the invention.

Figure 1:
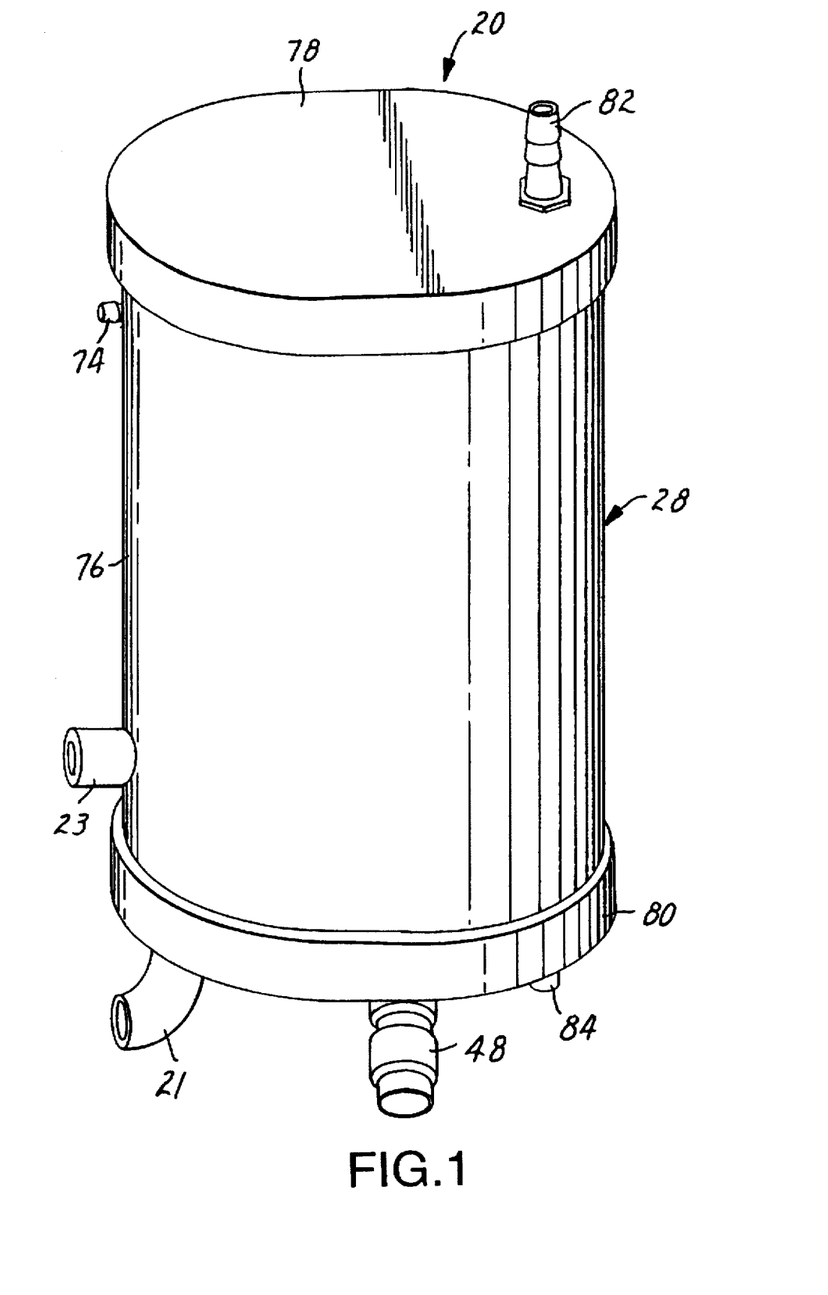
FIG. 1 is a perspective view of a blood oxygenator and heat exchanger of the invention.
Figure 2:
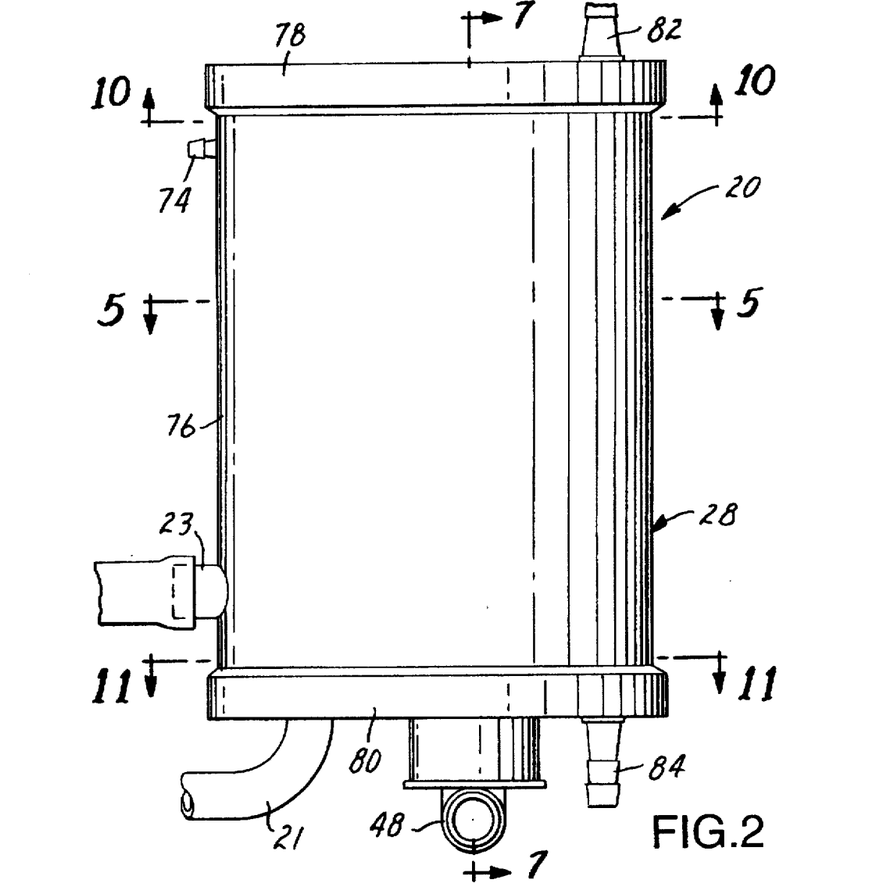
FIG. 2 is a side elevational view of the blood oxygenator and heat exchanger of FIG. 1.
Figure 3:
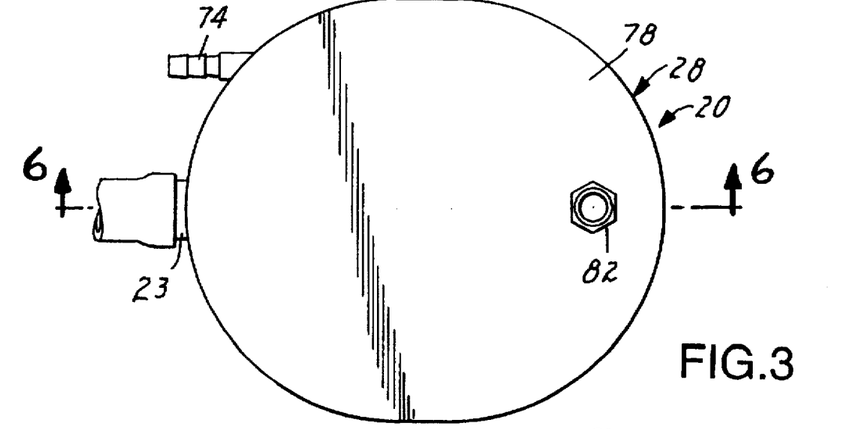
FIG. 3 is a top view of the blood oxygenator and heat exchanger of FIGS. 1 and 2.
Figure 4:
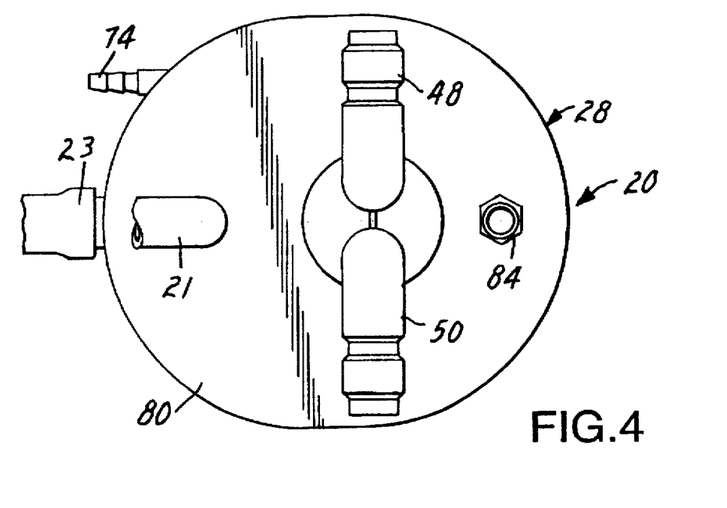
FIG. 4 is a bottom view of the blood oxygenator and heat exchanger of FIGS. 1-3.

The blood oxygenator and heat exchanger device 20 generally comprises a heat exchanger barrier 22, inlet manifold 24, blood oxygenating medium 26, a housing 28, and preferably a blood filtering medium 30. Venous blood enters the device 20 through a blood inlet port 21 preferably mounted on the bottom of the device 20, as illustrated in FIGS. 1 and 2, but which may alternatively be mounted on the top of the device. Oxygenated or arterial blood preferably exits the device through a blood outlet port 23 extending laterally outwardly from a side of the housing 28.

Figure 9:
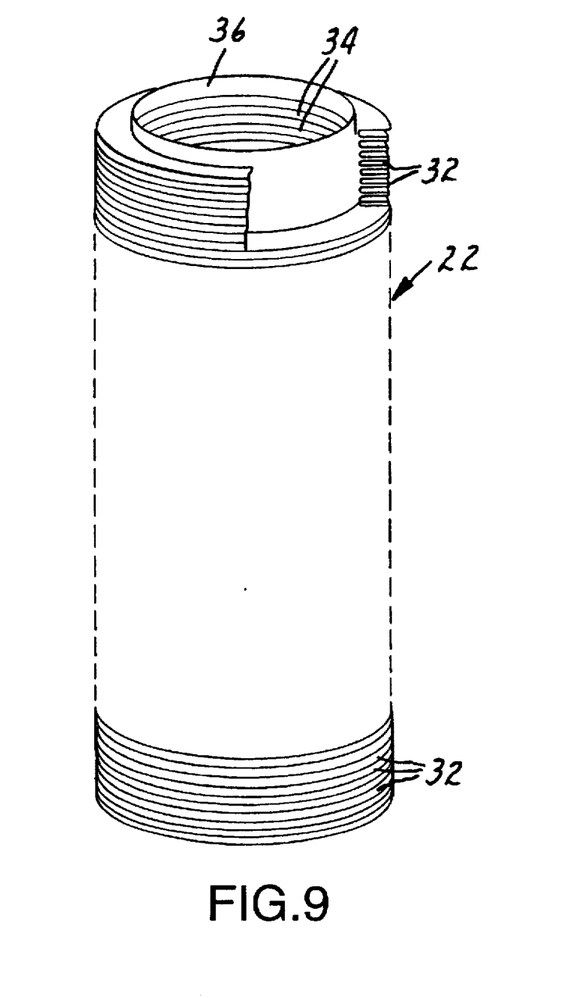
FIG. 9 is a perspective view of a heat exchanging barrier shown in FIGS. 5-7.

The heat exchanging barrier 22 separates blood and heat-exchanging fluid while permitting heat transfer across the barrier 22. As illustrated in FIG. 9, the heat exchanger barrier 22 preferably comprises a generally elongate and tubular metallic barrier 22 formed, for example, of stainless steel. The barrier 22 is elongate generally in the longitudinal direction of the device 22, with the longitudinal axis of the barrier 22 most preferably being parallel to the longitudinal direction of the device 22. As illustrated in FIG. 7A, the heat exchanger barrier 22 has an undulating wall 22 defining a plurality of "outer" channels 32 extending generally circumferentially around the outside of the heat exchanger barrier 22, and a plurality of "inner" channels 34 extending circumferentially around the lumen 36 of the heat exchanging barrier 22.

The outer channels 32 of the heat exchanger barrier 22 together form a blood flow passageway (also 32), and the inlet manifold 24 closely receives the heat exchanger barrier 22 so that the blood flow passageway 32 is substantially restricted to the channels 32. The inner channels 34 of the heat exchanger barrier 22 form a heat-exchanging fluid (e.g., water) passageway (also 34) through which heat exchanging fluid flows to either heat or cool blood flowing in the blood flow passageway 32. The undulating, channel-defining surface of the heat exchanging barrier 22 is believed to be helpful in maximizing heat transfer through the surface of the heat exchanging barrier 22.

Figure 6:
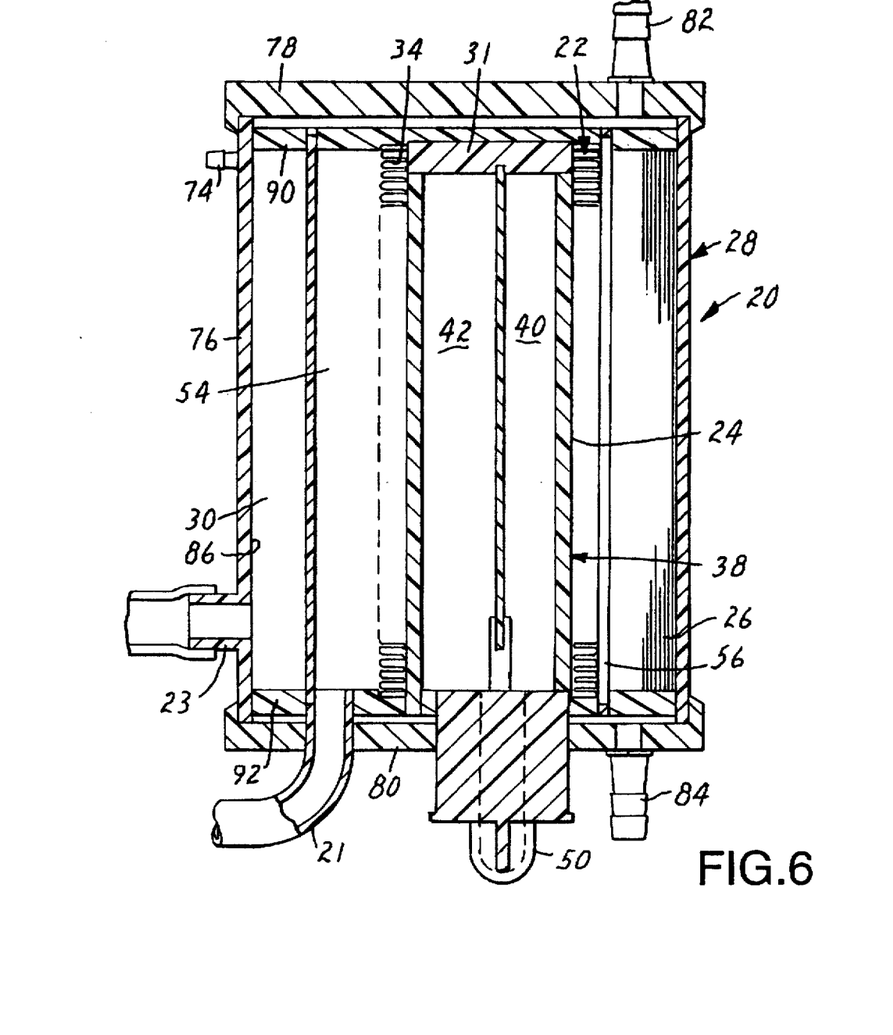
FIG. 6 is a cross-sectional view substantially along line 6—6 of FIG. 3.
Figure 7:
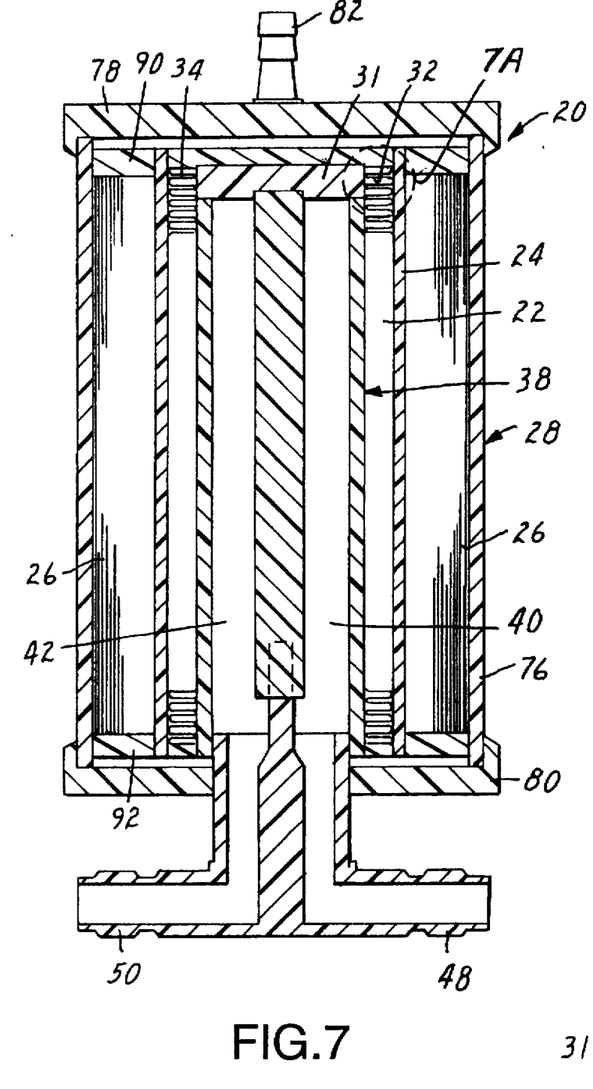
FIG. 7 is a cross-sectional view substantially along line 713 7 of FIG. 2.
Figure 7A:
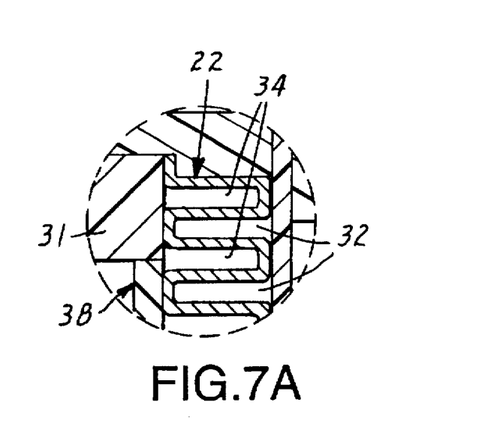
FIG. 7A is an enlarged area designated 7A in FIG. 7, illustrating details of the heat exchanger barrier.

As illustrated in FIGS. 6 and 7, one end cap 31 is provided covering the upper end of the lumen 36 of the barrier 22. The end cap 31 is sealed in potting compound 90 to seal the lumen 36 of the heat exchanger barrier 22, and serves to further separate the heat exchanging fluid circulating in the lumen 36 of the heat exchanger barrier 22 from the blood flow path outside the heat exchanger barrier 22. A second end cap (not shown) may be provided along the lower end of the lumen 36 of the barrier 22 but that end cap has been cut off of the example shown in the drawings to allow heat exchanging fluid to be supplied to and drained from the lumen 36 of the barrier 22 after the lower end of the blood oxygenating medium 26, blood filtering medium 30, inlet manifold 24, etc. have been sealed with potting compound 92 in the housing 28.

Figure 5:
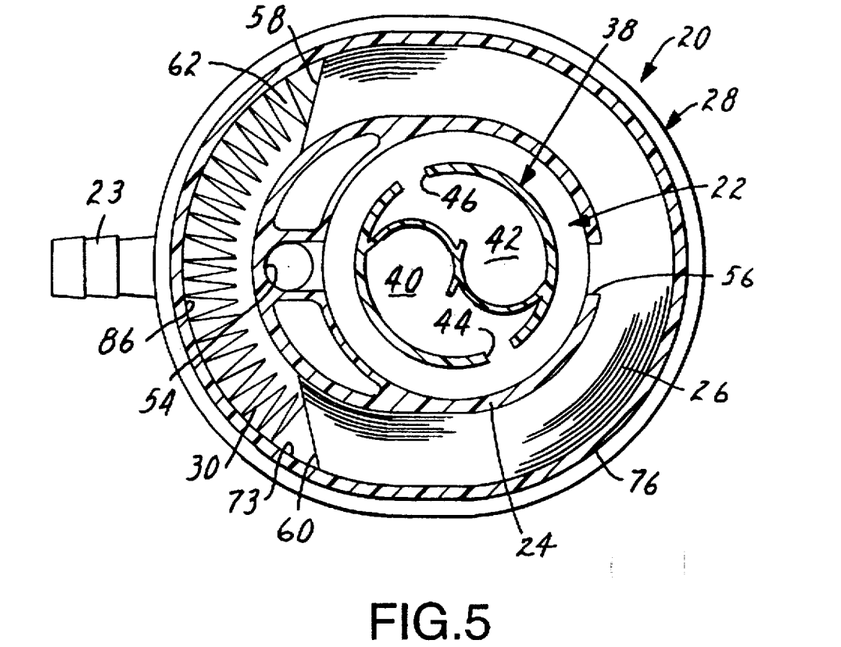
FIG. 5 is a cross-sectional view substantially along line 5—5 of FIG. 2.
Figure 5A:
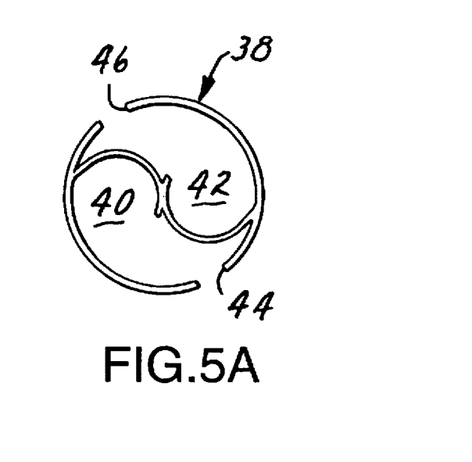
FIG. 5A is a end view of a heat-exchanger manifold shown in FIG. 5.

As illustrated in FIG. 5A, a heat-exchanger manifold 38 is preferably provided in the lumen 36 of the heat exchanger barrier 22 to force the heat exchanging fluid to flow through the inner channels 34. The heat-exchanger manifold 38 is generally elongate and cylindrical, and is closely received within the lumen 36 of the heat exchanger barrier 22 to define a passageway 34 for the heat exchanging fluid as being substantially within the inner channels 34 of the heat exchanging barrier 22. Since the heat-exchanger manifold 38 is closely received in the lumen 36 of the heat exchanger barrier 22, like the heat-exchanger barrier 22, the heat exchanger manifold 38 has a longitudinal axis that is generally parallel with the longitudinal direction of the device 22.

The heat-exchanger manifold 38 includes an inlet passageway 40 and outlet passageway 42, each having elongate slots 44 and 46, respectively, extending longitudinally along the heat-exchanger manifold and opening into the inner channels 34 of the heat exchanger barrier 22. Heat exchanging fluid enters the inner channels 34 through elongate slot 44, and travels circumferentially in both directions through the inner channels 34 until it exits the inner channels 34 through elongate slot 46. FIG. 7 shows the heat exchanging fluid inlet and outlet ports 48 and 50 on the housing 28, which supply and drain heat exchanging fluid from the inlet and outlet passageways 40 and 42.

Figure 8:
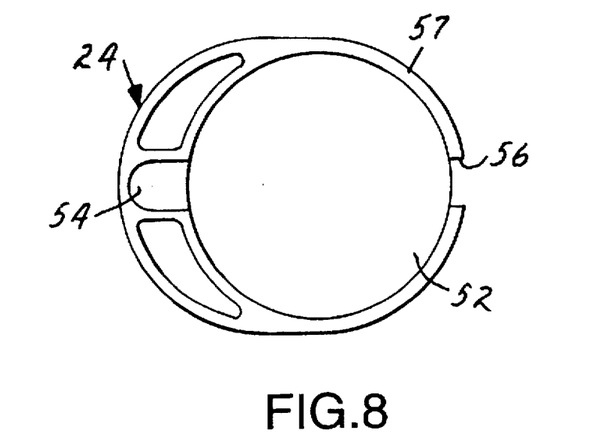
FIG. 8 is an end view of a inlet manifold shown in FIGS. 5-7.

The inlet manifold 24 is generally elongate in the longitudinal direction of the device 20, and has a generally rounded, oblong outer configuration in planes that are perpendicular to the longitudinal direction, as illustrated in FIG. 8. The inlet manifold 24 has a major generally cylindrical lumen 52 extending in the longitudinal direction that closely receives the heat exchanger barrier 22.

The inlet manifold 24 defines a blood inlet passageway 54 extending longitudinally along one side of the heat exchanger barrier 22, and a blood outlet slot 56 extending generally longitudinally along the opposite side of the heat exchanger barrier 22. The blood inlet passageway 54 has an elongate opening extending in the longitudinal direction of the device along the side of the heat exchanging barrier 22 to distribute incoming blood substantially along the length of the heat exchanger barrier 22. The outlet slot 56 extends substantially along the length of the heat exchanger barrier 22 so that blood flow through the outlet slot 56 remains distributed in the longitudinal direction within the device 20.

Incoming "venous" blood is brought from the blood inlet port 21 through the blood inlet passageway 54, and then travels in both directions circumferentially around the outer channels 32 of the heat exchanger barrier 22, and exits the inlet manifold 24 through the blood outlet slot 56. Most preferably, the walls 57 of the inlet manifold 24 are somewhat resiliently-flexible so that they can resiliently receive the heat exchanger barrier 22 within the lumen 52 to ease assembly and insure that blood flow is restricted to the outer channels 32 of the heat exchanger 22.

The blood oxygenating medium 26 is wrapped around the inlet manifold 24 so that blood flow through the outlet slot 56 of the inlet manifold 24 must pass through the blood oxygenating medium 26. The blood oxygenating medium 26 has opposite ends 58 and 60 that preferably define a gap 62 between the ends 58 and 60 along the outside surface of the inlet manifold 24 along the opposite side of the inlet manifold 24 from the blood outlet slot 56 of the inlet manifold 24. The gap 62 extends generally in the longitudinal direction of the device 20 substantially across the internal length of the device. Oxygenated blood exits the blood oxygenating medium 26 through the opposite ends 58 and 60 into the gap 62, traveling generally in the same direction as the blood did through the blood oxygenating medium 26. The blood oxygenating medium 26 preferably covers the outlet slot 56 of the inlet manifold 24, but alternatively the blood oxygenating medium 26 may be provided in two sections separated by a second gap (not shown) extending over the outlet slot 56 of the inlet manifold 24.

Figure 12:
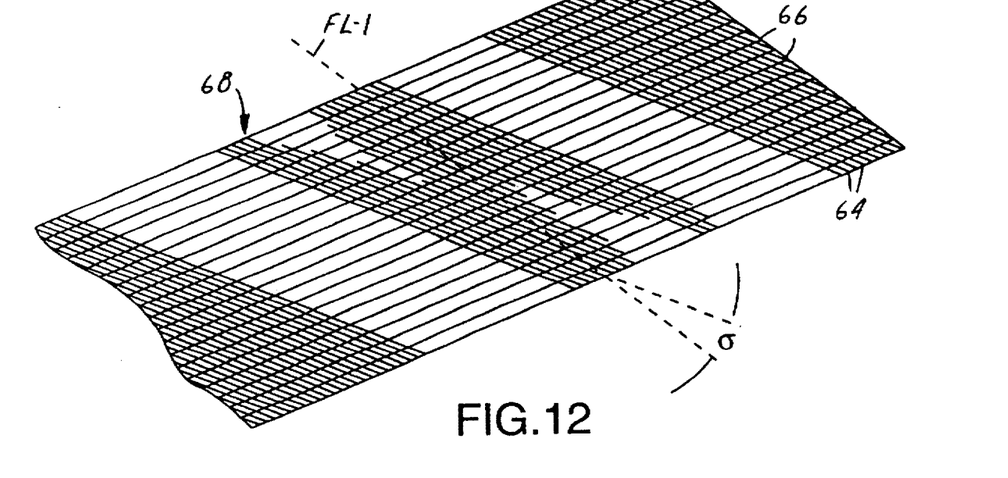
FIG. 12 is an side view of an elongate, generally continuous hollow fiber mat of the type to be formed into the blood oxygenating medium of FIGS. 5-7.
Figure 13:
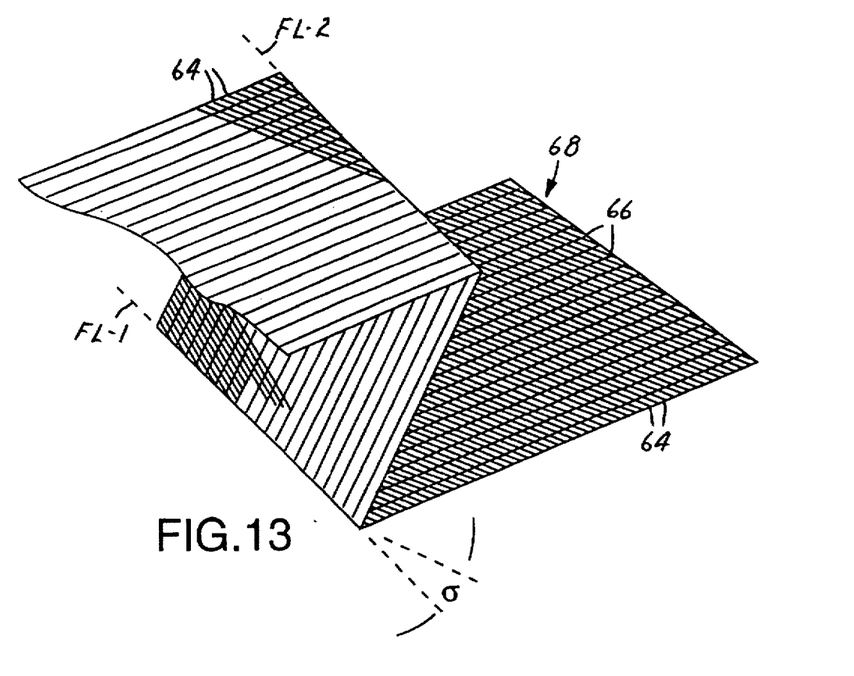
FIG. 13 is a side view of the hollow fiber mat of FIG. 12 being folded to form the blood oxygenating medium shown in FIGS. 5-7.
Figure 14:
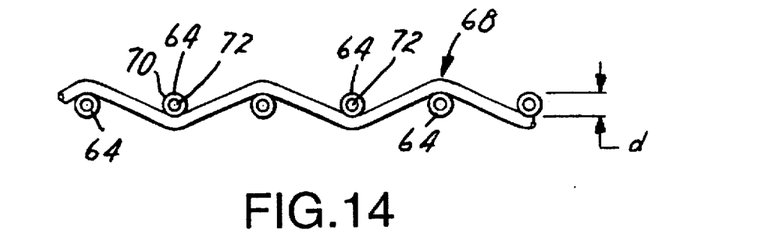
FIG. 14 is an enlarged side view of a small section of the mat of FIGS. 12-13, illustrating details of the hollow fiber and the weaving of a connecting fiber between the hollow fibers.

The blood oxygenating medium 26 is of the microporous hollow fiber membrane type, preferably comprising a plurality of polypropylene microporous hollow fibers 64 and a plurality of generally solid connecting fibers 66 interweaved in the form of a mat 68, as illustrated in FIGS. 12–14. For example, there may be approximately thirty hollow fibers 64 per linear inch (12 fibers/centimeter) of mat 68, and each hollow fiber 64 may have an outer diameter "d" of approximately 30 micrometers. The width of the hollow fiber mat 68 would preferably be about 6 or 6½ inches (150–165 mm), which is substantially the same as the internal length of the device 20. As illustrated in FIG. 14, each hollow fiber 64 has a microporous tubular wall 70 that is generally microporous to allow transfer of gas but not liquid through the wall 70, so that oxygen may pass outwardly from the lumen 72 through the wall 70 into blood circulating outside the hollow fiber 64, and so that carbon dioxide may pass inwardly from the blood through the wall 70 into the lumen 72 so that it may be carried away.

Preferably, the hollow fibers 64 extend in a direction that is almost but not quite perpendicular to the overall direction of blood flow through the blood oxygenating medium 26. Most preferably, the hollow fibers 64 extend at an oblique angle of approximately 75–89 degrees (e.g., 85 degrees) with respect to the overall direction of blood flow through the blood oxygenating medium 26.

A preferred example of the blood oxygenating medium 26 and a method of making the blood oxygenating medium is described in a co-assigned U.S. patent application on "Multilayer Hollow Fiber Body" by Ronald J. Leonard filed on the same day as this application under Attorney Docket No. 50997 USA 3A, with Express Mail certificate, Label No. EH086388681 US, dated Nov. 30, 1995, which is hereby incorporated herein by reference. Suitable mats for use in the oxygenating medium 26 are available in roll-form under the trade designation "OXYPHAN™" membranes from the Fibers Division of Akzo Nobel Faser AG, Wuppertal, Germany, or under the trade designation "CELGARD™ hollow fiber array" from the Separations Products Division of Hoechst Celanese Corporation, Charlotte, N.C.

As described in the co-assigned U.S. patent application on "Multilayer Hollow Fiber Body" by Ronald J. Leonard and illustrated in FIGS. 12–14 herein, the hollow fibers 64 are disposed at substantially regular intervals, and the connecting fibers 66 are preferably disposed at substantially regular intervals. As used herein, the term "regular intervals" does not require equal intervals, although equal intervals are preferred. Rather, the term "regular intervals" means, for example, that the hollow fibers 64 are generally parallel to one another in the mat 68 before the mat 68 is folded. As will be discussed below, after the mat 68 is folded, the hollow fibers 64 of one ply will be parallel to one another but will cross the hollow fibers 64 of adjacent plies.

As used herein with respect to the mat 68, the terms "longitudinal", "longitudinally" or "direction of elongation" refer to the elongate or continuous direction of the mat 68, and the terms "lateral" or "laterally" refer to the direction across the width of the mat 68, which is perpendicular to the longitudinal direction of the mat 68. The term "length" in connection with the mat 68 refers to a distance in the longitudinal direction of the mat 68. The term "width" of the mat 68 refers to the distance laterally across the mat 68. As used herein, the terms "elongate" or "direction of elongation" do not imply or require the mat to be stretched; they simply refer to the longer dimension of the mat.

The connecting fibers 66 extend generally in the longitudinal direction of the mat 68, and the hollow fibers 64 extend at an oblique angle σ relative to the lateral direction of the mat. As used herein, the term "oblique angle" refers to an angle other than zero, 90, 180, 270 or 360 degrees. The oblique angle a is preferably 1–15 degrees (e.g., 5 degrees). The hollow fibers 64 can also be considered as extending at an oblique angle relative to the longitudinal direction of the mat 68, which is equal to ninety minus the oblique angle σ. Thus, the hollow fibers 64 preferably extend at an oblique angle of approximately 75–89 degrees (e.g., 85 degrees) relative to the longitudinal direction of the mat 68. The oblique angle can be formed in the original production of the mat 68, or by flexing or displacing one edge of the mat 68 longitudinally relative to the opposite edge of the mat 68.

Most preferably, the mat 68 is provided in roll-form with the hollow fibers 64 pre-skewed at the desired oblique angle. Alternatively, the mat 68 could be provided with the hollow fibers 64 arranged generally perpendicularly to the longitudinal direction of the mat 68, and the first ply of the mat 68 could be held in a folding apparatus, of the type described in the co-assigned U.S. patent application on "Multilayer Hollow Fiber Body and Method of Making" by Ronald J. Leonard, with the hollow fibers 64 skewed at the desired oblique angle, or the mat 68 could be processed between the mat-supply roll and the folding apparatus to orient the hollow fibers 64 at the desired oblique angle.

As illustrated in FIG. 14, the mat 64 is repeatedly folded over on itself along fold lines, e.g., FL-1, FL-2, . . . , FL-N, that are disposed at an oblique angle relative to the hollow fibers 64. "N", for example, could equal approximately 50 fold lines. The repeatedly folded mat 68 forms a multilayer hollow fiber body (also 26) in which the hollow fibers 64 of any ply of the body 26 are disposed so as to cross the hollow fibers 64 of an adjacent successive ply of the body 64. Preferably, the fold lines FL-1, FL-2, etc., are generally parallel to one another, and extend generally laterally across the mat 68 so that they are at the oblique angle σ relative to the hollow fibers 64. The result is that the hollow fibers 64 of one ply cross over the previous ply at an oblique angle 2σ. Opposite edges 58 and 60 and of the body 26 are defined by the fold lines FL-1, FL-2, . . . , FL-N, of the mat 64. Most preferably, the mat 64 is not crimped along the fold lines, FL-1, FL-2, . . . , FL-N, so that gas may flow through any hollow fibers 64 that extend past the fold lines. The hollow fiber body 26 is designed to promote mixing of blood flow around the hollow fibers 64 without excessive pressure drop.

Most preferably, the distance between the fold lines, FL-1, FL-2, . . . , FL-N, along any ply is the same as the distance between the fold lines along any other ply. This arrangement is such that, when the multilayer hollow fiber body 26 is wrapped around the inlet manifold 24, the plies progressively leave a wider gap 62 between the opposite ends 58 and 60 in the direction outwardly from the inlet manifold 24 toward the housing 28, as illustrated in FIG. 5. This feature provides certain advantages. For example, since the outer plies do not extend as far around the device 20 as do the inner plies, they open up a larger space between the hollow fiber body 26 and the preferred blood filter 30 in the direction toward the wall 73 of the housing 28 that can facilitate venting of gas upstream of the blood filter 30 or use of an optional bypass port 74 to bypass the blood filter 30.

The tapered configuration of the opposite ends 58 and 60 also means that the mat 68 is less restricted in the lateral direction of the device 20 along and generally adjacent the fold lines FL-1, FL-2, . . . , FL-N. This reduces any constriction of the lumens 72 of the hollow fibers 64 across the fold lines and helps maintain a flow path through the lumens 72 of the hollow fibers 64 that cross the fold lines. In addition, care should be taken during the folding process not to crimp the hollow fibers 64 along the fold lines FL-1, FL-2, . . . , FL-N so that gas may freely flow through the hollow fibers 64 that cross the fold line.

Preferably, the blood filtering medium 30 is disposed within the gap 62 between the blood oxygenating medium 26 and the outlet manifold 76 to filter blood before the blood exits the housing 20 through the blood outlet port 23. For example, the blood filtering medium 30 comprises a conventional pleated filter element (also 30) that is pleated along fold lines that extend generally in the longitudinal direction of the device 20. The filter element 30 extends substantially along the entire internal length of the device 20.

The filter element 30 is arranged so that blood exiting the blood oxygenating medium 26 must pass through the filter element 30 before reaching the outlet port 23. This can be accomplished by sealing the filter element to the internal wall 73 of the housing 28 along the periphery of the filter element 30 and by sealing the longitudinal edges of the filter element 30 in potting compound. Alternatively, this can be accomplished by pleating only the portion of the filter element 30 shown in FIG. 5, and wrapping large lateral end portions around the oxygenating medium 26 so that they extend substantially completely around the outside ply of the oxygenating medium 26 along the internal wall 73 of the housing 28, and sealing the longitudinal edges of the filter element 30 in potting compound along the longitudinal ends of the internal area of the device 20. In any event, space is provided between the filter element 30 and the inlet manifold 24 so that blood may freely communicate between the opposite ends 58 and 60 of the blood oxygenating medium 26 along the upstream side of the filter element 30. This allows blood to reach the inner pleats of the filter element 30, and also facilitates venting of gas from the upstream side of the filter element 30.

Preferably, at least one vent port 74 is provided on the housing 28 adjacent the top of the housing 28 in fluid communication with the gap 62 on the upstream side of the blood filtering medium 30 for venting gas upstream of the blood filtering medium 30. A single vent 74 is believed to be adequate to vent along the upstream side of the blood filtering medium 30, since the filtering medium 30 does not fill the entire width of the gap 62 between the wall 73 of the housing 28 and the inlet manifold 24. The vent port 74 opens through the housing wall 73 into the gap 62 below and closely adjacent the surface of the potting compound 90 so that the last bit of any gas collecting upstream of the filter element 30 can be removed.

A bypass means may optionally be provided for bypassing the blood filtering medium 30 if the blood filtering medium 30 becomes clogged to allow blood to exit the housing 28 without passing through the blood filtering medium 30. For example, a bypass port (not shown) may be provided on the housing 28 in fluid communication with the gap 62 between the opposite ends 58 and 60 of the blood oxygenating medium 26 and the blood filtering medium 30. The bypass port would be identical to the outlet port 23 except that the bypass port would open into the gap 62 on the upstream side rather than the downstream side of the filter element 30. The vertical level of the bypass port would be similar to the level of the outlet port 23. Details of how tubing would be connected to such a bypass port to facilitate switching between the normal outlet port 23 and the bypass port are shown in allowed, co-assigned U.S. patent application Ser. No. 08/142,809, filed Oct. 25, 1993, which is hereby incorporated herein by reference. See, also, PCT International Publication No. WO 95/11709.

The blood oxygenating medium 26, inlet manifold 24, heat exchanger barrier 22 and blood filtering medium 30 are closely received in the housing 28. The housing 28 comprises a main generally tubular portion 76 having a generally oblong cross section that, while larger than the oblong cross section of the inlet manifold 24, corresponds to that cross section so that the distance between the internal wall 73 of the portion 76 of the housing 28 and the outer wall of the inlet manifold 24 remains generally constant throughout the device 20.

One way to assemble the blood oxygenating medium 26, inlet manifold 24, heat exchanger barrier 22 and blood filtering medium 30 into the portion 76 of the housing 28 is to use the wrap-around version of the filter element 30, or a separate sheet (not shown) wrapped around these components, to slightly compress the blood oxygenating medium 26 and insert the blood oxygenating medium 26, inlet manifold 24, heat exchanger barrier 22 and blood filtering medium 30 into the tubular portion 26 of the housing 28.

The filter element 30 and blood oxygenating medium 26 then relax to fill the space and reduce compression of the blood oxygenating medium 26 within the tubular portion 76 of the housing 22. Potting compound 90, 92 is then used to seal along the longitudinal ends of the assembly, e.g., to seal between the hollow fibers 64 of the blood oxygenating medium. A cut is then made through each section of cured potting compound 90, 92 in horizontal planes (relative to the intended use of the device 20) to open up the ends of the lumens 72 of the hollow fibers 64. The ends of the hollow fibers 64 of this type are conventionally supplied sealed so that potting compound does not fill the lumens 72 of the hollow fibers 64, and the closed ends are cut-off when the cut is made through the potting compound.

Figure 10:
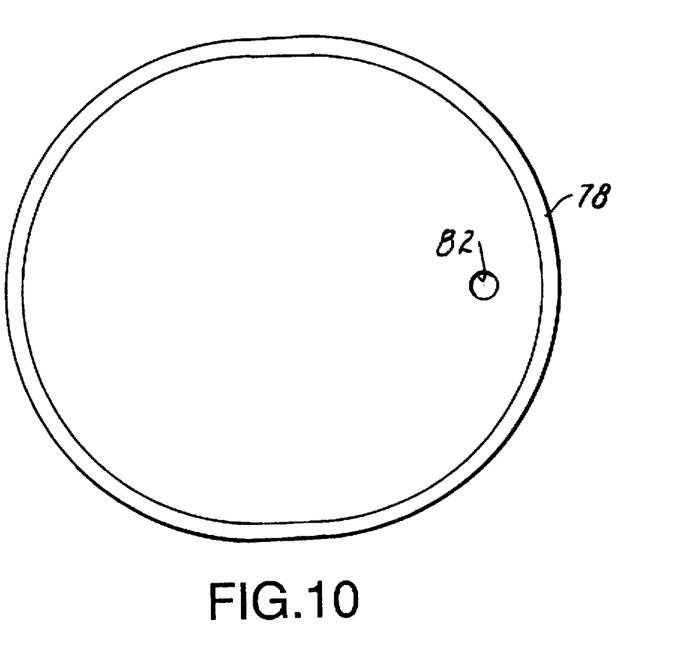
FIG. 10 is a cross-sectional view substantially along line 10—10 of FIG. 2, illustrating the configuration of the inside of a top end cap of the blood oxygenator and heat exchanger.

Manifold end caps 78 and 80 (FIGS. 10 and 11) are mounted on the opposite ends of the tubular portion 76 of the housing 22, and provide inlet and outlet gas manifolds for the blood oxygenating medium 26. The manifold end caps 78 and 80 provide gas ports 82 and 84 in fluid communication with the lumens 72 of the hollow fibers 64, as well as including the heat exchanging inlet and outlet ports 48 and 50 in the bottom manifold end cap 80.

Figure 11:
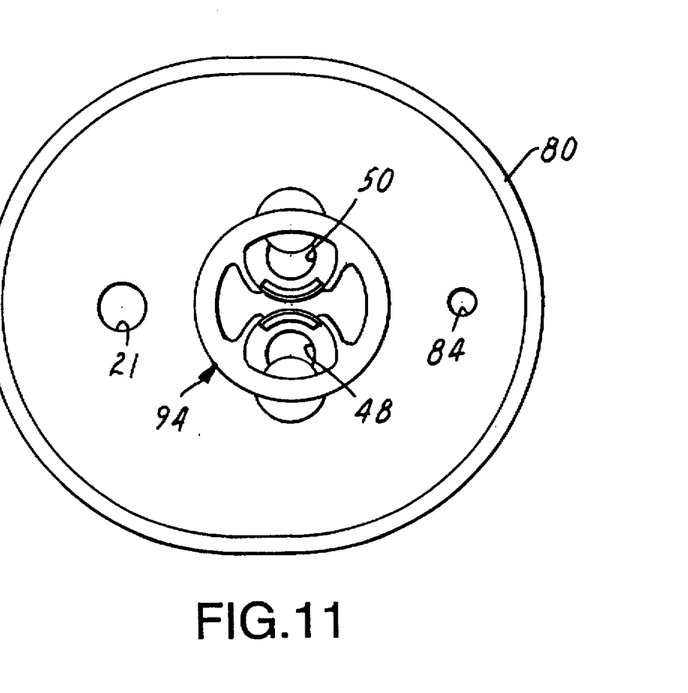
FIG. 11 is a cross-sectional view substantially along line 11—11 of FIG. 2, illustrating the configuration of the inside of a bottom end cap of the blood oxygenator and heat exchanger.

The bottom manifold end cap 80 is configured at 94 to help seal between the heat exchanging fluid path and the gas path, and to direct incoming heat exchanging fluid from heat exchanging fluid inlet port 48 to passageway 40 of the heat-exchanger manifold 38, and to direct outgoing heat exchanging fluid from the passageway 42 of the heat exchanger manifold 38 to the heat exchanging fluid outlet port 50. The configured section 94 of the bottom manifold end cap 80 seals against the potting compound 92 and lower end of the lumen 36 of the heat exchanger barrier 22.

An outlet manifold 86 extends longitudinally along one side of the housing 28 along the upstream side of the filter element 30 generally opposite the blood outlet slot 56 of the inlet manifold 24. The blood outlet port 23 is in fluid communication with the outlet manifold 86, which may merely constitute the area between the downstream surface of the filter element 30 and the outlet port 23. Alternatively, the outlet manifold 86 could comprise a tapered slot (not shown) that collects blood along the downstream side of the filter element 30 to direct that blood to the outlet port 23. The outlet manifold 86 and the blood outlet slot 56 of the inlet manifold 24 define a blood flow path through the blood oxygenating medium 26 extending around the inlet manifold 24 between the blood outlet slot 56 of the inlet manifold 24 and the outlet manifold 86 of the housing 22.

The device 20 described above provides a fairly direct blood flow path between the various elements, e.g., the heat exchanger barrier 22, blood oxygenating medium 26 and blood filtering medium 30, without intervening collection and distribution manifolds. The blood flow remains distributed in the longitudinal direction of the device 20 between the blood inlet passageway 54 and the blood outlet manifold 86.

There is normally pressure loss through blood oxygenating mediums. The blood oxygenating medium 26 reduces this pressure loss compared to many designs by allowing blood to flow out through the opposite ends 58 and 60 in the same general direction of blood flow through the blood oxygenating medium 26. In addition, the tapered configuration of the opposite ends 58 and 60 of the blood oxygenating medium 26 is believed to facilitate flow out through the opposite ends 58 and 60.

The device 20 is described as having a particular orientation, with top and bottom ends, etc., both because that is the preferred orientation and to simplify the description. The device, however, with some modification, can be made in other orientations, for example, by having the blood inlet ports 21 and/or heat exchanging fluid ports 48 and 50 mounted on the top manifold cap. As various orientations are possible, it is intended that the invention as set forth in the claims not be limited to the particular orientation described.

As various changes could be made in the above constructions without departing from the scope of the invention as defined in the claims, it is intended that all matter contained in the above description or shown in the accompanying drawings be interpreted as illustrative and not in a limiting sense.

I claim:

1. An integral blood oxygenator and heat exchanger for oxygenating and heating or cooling a patient's blood during heart bypass surgery, the blood oxygenator and heat exchanger comprising:

a generally elongate, generally tubular heat exchanger barrier for separating blood and heat-exchanging fluid while permitting heat transfer across the barrier;

a generally elongate inlet manifold closely receiving the heat exchanger barrier, the inlet manifold defining a blood inlet passageway extending longitudinally along one side of the heat exchanger barrier, and a blood outlet slot extending generally longitudinally along the opposite side of the heat exchanger barrier, the blood inlet passageway and blood outlet slot defining a blood flow passageway extending generally circumferentially around the heat exchanger barrier;

a blood oxygenating medium comprising a plurality of plies of a mat, each ply of the mat comprising porous hollow fibers through which oxygen flows to oxygenate blood flowing around the porous hollow fibers, the blood oxygenating medium being wrapped around the inlet manifold so that blood exiting the blood outlet slot must flow through the blood oxygenating medium; and a housing closely receiving the blood oxygenating medium, inlet manifold and heat exchanger barrier, the housing defining an outlet manifold extending longitudinally along one side of the housing generally opposite the blood outlet slot of the inlet manifold, thereby defining a blood flow path through the blood oxygenating medium extending around the inlet manifold between the blood outlet slot of the inlet manifold and the outlet manifold of the housing, the housing having a blood outlet in fluid communication with the outlet manifold and a blood inlet in fluid communication with the blood inlet passageway of the inlet manifold.

2. An integral blood oxygenator and heat exchanger according to claim 1 further comprising a blood filtering medium disposed between the blood oxygenating medium and the outlet manifold to filter blood before the blood exits the housing through the outlet manifold and blood outlet.

3. An integral blood oxygenator and heat exchanger according to claim 2 wherein the blood oxygenating medium has opposite ends defining a gap extending longitudinally along the side of the inlet manifold generally opposite the blood outlet slot, the blood filtering medium being disposed within the gap.

4. An integral blood oxygenator and heat exchanger according to claim 3 further comprising bypass means for bypassing the blood filtering medium if the blood filtering medium becomes clogged to allow blood to exit the housing without passing through the blood filtering medium.

5. An integral blood oxygenator and heat exchanger according to claim 4 wherein the bypass means comprises a bypass port on the housing in fluid communication with the gap between the opposite ends of the blood oxygenating medium and the blood filtering medium.

6. An integral blood oxygenator and heat exchanger according to claim 3 further comprising at least one vent port on the housing in fluid communication with the gap between the opposite ends of the blood oxygenating medium and the blood filtering medium for venting gas upstream of the blood filtering medium.

7. An integral blood oxygenator and heat exchanger according to claim 6 wherein the blood filtering medium comprises a pleated filter element.

8. An integral blood oxygenator and heat exchanger according to claim 1 wherein the blood oxygenating medium has opposite ends defining a gap extending longitudinally along the side of the inlet manifold generally opposite the blood outlet slot, the blood oxygenating medium covering the blood outlet slot of the inlet manifold such that blood enters the blood oxygenating medium from the blood outlet slot intermediate the opposite ends of the blood oxygenating medium, travels through the blood oxygenating medium in opposite directions and exits the blood oxygenating medium through the opposite ends of the blood oxygenating medium.

9. An integral blood oxygenator and heat exchanger according to claim 8 wherein the mat comprises a single hollow fiber mat;

the porous hollow fibers comprising a plurality of hollow fibers disposed at regular intervals, the single mat further comprising a plurality of connecting fibers holding the hollow fibers; and the mat being repeatedly folded over on itself along fold lines, each of which is at an oblique angle to the hollow fibers, to form a multilayer hollow fiber body in which the hollow fibers of any ply of the multilayer hollow fiber body are disposed so as to cross the hollow fibers of an adjacent successive ply of the multilayer hollow fiber body.

10. An integral blood oxygenator and heat exchanger according to claim 9 wherein the mat is generally elongate, the hollow fibers extending at an oblique angle with respect to the direction of elongation of the mat, the fold lines being generally parallel to one another and generally perpendicular to the direction of elongation of the mat.

11. An integral blood oxygenator and heat exchanger according to claim 10 wherein the oblique angle between the hollow fibers and the fold lines is between approximately 1–15 degrees.

12. An integral blood oxygenator and heat exchanger according to claim 10 wherein the connecting fibers are disposed at regular intervals and extend generally in the direction of elongation of the mat, the connecting fibers being interweaved with the hollow fibers to hold the fibers in the mat.

13. An integral blood oxygenator and heat exchanger according to claim 9 wherein the multilayer hollow fiber body has opposite ends defining a gap extending longitudinally along the side of the inlet manifold generally opposite the blood outlet slot; the integral blood oxygenator and heat exchanger further comprising:

a blood filtering medium disposed within the gap between the multilayer hollow fiber body and the outlet manifold to filter blood before the blood exits the housing through the outlet manifold and blood outlet; and at least one vent port on the housing in fluid communication with the gap between the opposite ends of the blood oxygenating medium and the blood filtering medium for venting gas upstream of the blood filtering medium.

14. An integral blood oxygenator and heat exchanger according to claim 13 wherein the distance between the fold lines along any ply is the same as the distance between the fold lines along any other ply, the arrangement being such that, when the multilayer hollow fiber body is wrapped around the inlet manifold, the plies progressively leave a wider gap between the opposite ends in the direction outwardly from the inlet manifold toward the housing.

15. An integral blood oxygenator and heat exchanger according to claim 8 wherein the heat exchanger barrier comprises a generally tubular metallic barrier having an undulating wall defining a plurality of channels that together form the blood flow passageway.

16. An integral blood oxygenator and heat exchanger according to claim 15 wherein the plurality of channels extend generally circumferentially around the metallic barrier, the inlet manifold closely receiving the heat exchanger barrier so that the blood flow passageway is substantially restricted to the channels.

17. An integral blood oxygenator, heat exchanger and blood filter device for oxygenating and heating or cooling a patient's blood during heart bypass surgery, the unit comprising:

a heat exchanger barrier for separating blood and heat-exchanging fluid while permitting heat transfer across the barrier;

a manifold receiving the heat exchanger barrier, the manifold defining a blood inlet and a blood outlet defining a blood flow passageway extending along the heat exchanger barrier;

a blood oxygenating medium wrapped around the manifold so that blood flow through the outlet of the manifold must pass through the blood oxygenating medium, the blood oxygenating medium having opposite ends defining a gap between the ends along the outside of the manifold;

a blood filtering medium disposed within the gap between the opposite end of the blood oxygenating medium to filter blood exiting the blood oxygenating medium, the blood filtering medium having upstream and downstream sides; and a housing for the blood filtering medium, blood oxygenating medium, manifold and heat exchanger barrier, the housing having a blood outlet in fluid communication with the downstream side of the blood filtering medium, thereby defining a blood flow path through the blood oxygenating medium and blood filtering medium extending around the manifold between the blood outlet of the manifold and the blood outlet of the housing.

18. A device according to claim 17 wherein the blood oxygenating medium comprises a single hollow fiber mat having a plurality of plies, the single hollow fiber mat comprising a plurality of hollow fibers disposed at regular intervals, and a plurality of connecting fibers holding the hollow fibers;

the mat being repeatedly folded over on itself along fad lines, each of which is at an oblique angle to the hollow fibers, to form a multilayer hollow fiber body in which the hollow fibers of any ply of the multilayer hollow fiber body are disposed so as to cross the hollow fibers of an adjacent successive ply of the multilayer hollow fiber body.

19. A device according to claim 18 wherein the mat is generally elongate, the hollow fibers extending at an oblique angle with respect to the direction of elongation of the mat, the fold lines being generally parallel to one another and generally perpendicular to the direction of elongation of the mat; the connecting fibers being disposed at regular intervals and extending generally in the direction of elongation of the mat, the connecting fibers being interweaved with the hollow fibers to hold the fibers in the mat; the oblique angle between the hollow fibers and the fold lines being between approximately 1-15 degrees.

20. A device according to claim 18 further comprising at least one vent port on the housing in fluid communication with the gap between the opposite ends of the blood oxygenating medium and the blood filtering medium for venting gas upstream of the blood filtering medium.

21. A device according to claim 20 wherein the distance between the fold lines along any ply is the same as the distance between the fold lines along any other ply, the arrangement being such that, when the multilayer hollow fiber body is wrapped around the manifold, the plies progressively leave a wider gap between the opposite ends in the direction outwardly from the manifold toward the housing.

22. A device according to claim 20 further comprising a bypass port on the housing in fluid communication with the gap between the opposite ends of the blood oxygenating medium and the blood filtering medium for bypassing the blood filtering medium if the blood filtering medium becomes clogged to allow blood to exit the housing without passing through the blood filtering medium.

23. A device according to claim 17 wherein the blood oxygenating medium covers the outlet of the manifold.

24. An integral blood oxygenator and heat exchanger for oxygenating and heating or cooling a patient's blood during heart bypass surgery, the blood oxygenator and heat exchanger comprising:

a heat exchanger;

an inlet manifold receiving the heat exchanger, the inlet manifold forming a blood inlet passageway and a blood outlet slot defining a blood flow passageway through the heat exchanger;

a blood oxygenating medium having opposite ends and being wrapped around the inlet manifold such that (a) the opposite ends define a gap extending along the side of the inlet manifold generally opposite the blood outlet slot, and (b) the blood oxygenating medium covers the blood outlet slot intermediate the opposite ends of the blood oxygenating medium, so that blood enters the blood oxygenating medium from the blood outlet slot intermediate the opposite ends of the blood oxygenating medium, travels through the blood oxygenating medium in opposite directions and exits the blood oxygenating medium through the opposite ends of the blood oxygenating medium; and a housing receiving the blood oxygenating medium, inlet manifold and heat exchanger barrier, the housing having a blood outlet in fluid communication with the gap formed between the opposite ends of the blood oxygenating medium, and a blood inlet in fluid communication with the blood inlet passageway of the inlet manifold.

25. An integral blood oxygenator and heat exchanger according to claim 24 wherein the opposite ends of the blood oxygenating medium are tapered in the direction away from the inlet manifold.

* * * * *

UNITED STATES PATENT AND TRADEMARK OFFICE
CERTIFICATE OF CORRECTION

PATENT NO.: 5,762,868

DATED: June 9, 1998

INVENTOR(S): Ronald J. Leonard

It is certified that error appears in the above-identified patent and that said Letters Patent is hereby corrected as shown below:

Col. 13, line 51, "fad" should read --fold--.

Signed and Sealed this

Seventeenth Day of November, 1998

*Attest:*

BRUCE LEHMAN

*Attesting Officer*      *Commissioner of Patents and Trademarks*